United States Patent [19]

Carpentier et al.

[11] Patent Number: 4,917,698
[45] Date of Patent: Apr. 17, 1990

[54] MULTI-SEGMENTED ANNULOPLASTY RING PROSTHESIS

[75] Inventors: Alain Carpentier, Paris, France; Hung L. Lam, Norco; Than Nguyen, Huntington Beach, both of Calif.

[73] Assignee: Baxter International Inc., Deerfield, Ill.

[21] Appl. No.: 290,001

[22] Filed: Dec. 22, 1988

[51] Int. Cl.$^4$ ................................. A61F 2/24
[52] U.S. Cl. ........................................ 623/2
[58] Field of Search ............... 623/2; 446/327, 371

[56] References Cited

U.S. PATENT DOCUMENTS

| | | | |
|---|---|---|---|
| 179,263 | 4/1922 | Amberg | 446/371 |
| 2,433,555 | 12/1947 | Hulse | 446/327 |
| 3,656,185 | 4/1972 | Carpentier | 623/2 |
| 4,042,979 | 8/1977 | Angell | 623/2 |
| 4,164,046 | 8/1979 | Cooley | 623/2 |
| 4,261,342 | 4/1981 | Aranguren Duo | 623/2 |
| 4,290,151 | 9/1981 | Massana | 623/2 |
| 4,489,446 | 12/1984 | Reed | 623/2 |

Primary Examiner—Richard J. Apley
Assistant Examiner—Stephanie L. Iantorno
Attorney, Agent, or Firm—Michael C. Schiffer

[57] ABSTRACT

A ring prosthesis which provides different flexibilities at various points about the circumference of an associated heart valve. Specifically, the annuloplasty ring prosthesis of the invention includes a segmented body formed by two or more segments. The individual segments form a body which is substantially circular and shaped proportional to fit about the annulus of the associated heart valve. The individual segments are held in position with respect to each by a flexible joint. This flexible joint is formed by covering the segments with a flexible material which fits snugly about the segments. The cover is tied off between the adjacent segments to further restrain movement of the segments with respect to each other.

17 Claims, 1 Drawing Sheet

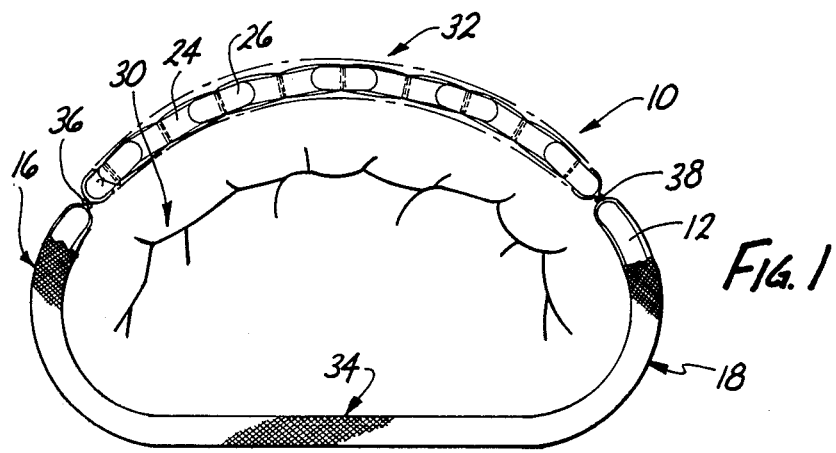
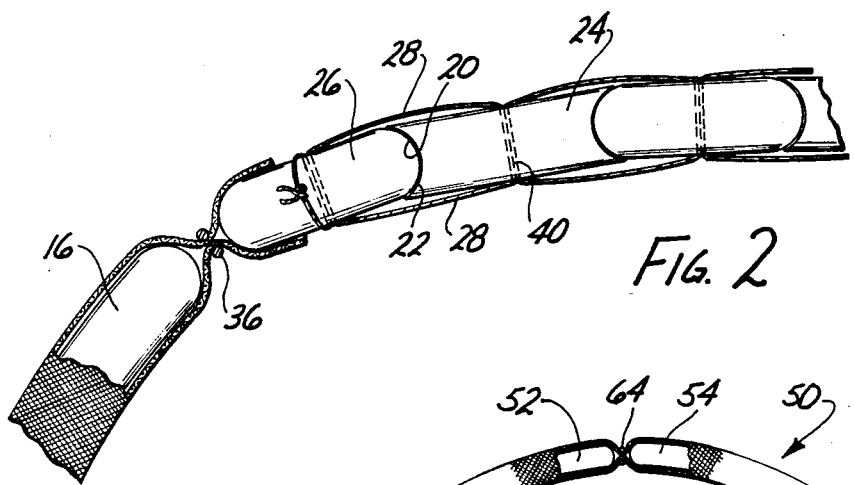
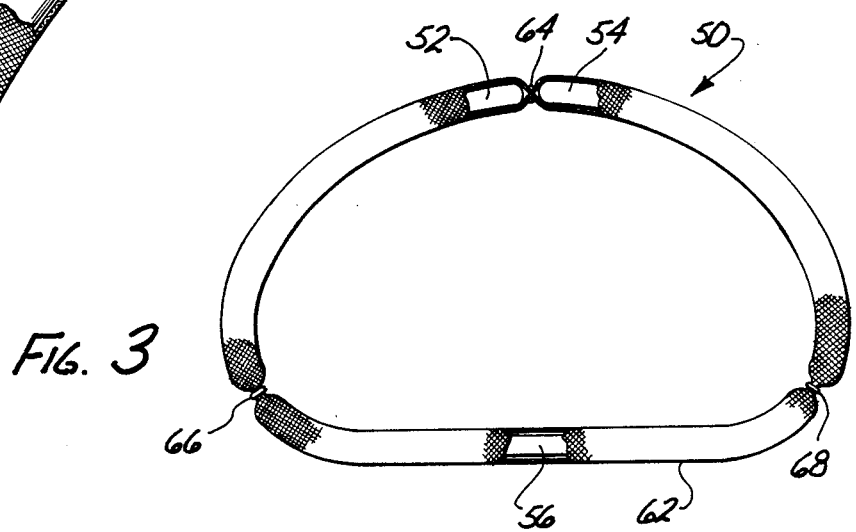

MULTI-SEGMENTED ANNULOPLASTY RING PROSTHESIS

BACKGROUND OF THE INVENTION

The present invention relates to a support for a natural human heart which may be used for the surgical correction of a deformed heart valve, and in particular a dilated heart valve.

The human heart generally includes four valves with the more critical of these valves being the tricuspid valve. The tricuspid valve is located in the right atrioventricular opening. The other important valve is the mitral valve which is located in the left atrioventricular opening. Both of these valves are intended to prevent regurgitation of blood from the ventricle into the atrium when the ventricle contracts. In preventing blood regurgitation, both valves must be able to withstand considerable back pressure as the ventricle contracts. The valve cusps are anchored to the muscular wall of the heart by delicate but strong fibrous cords in order to support the cusps during ventricular contraction. Furthermore, the geometry of the heart valves ensures that the cusps overlie each other to assist in controlling the regurgitation of the blood during ventricular contraction.

Diseases and certain natural defects to heart valves can impair the functioning of the cusps in preventing regurgitation. For example, certain diseases cause the dilation of the heart valve annulus. This dilation results in the distortion of the valve geometry or shape displacing one or more of the valve cusps from the center of the valve. The displacement of the cusps away from the center of the valve results in an ineffective closure of the valve during ventricular contraction. This results in the regurgitation or leakage of blood during ventricle contraction. Diseases such as rheumatic fever or bacterial inflammations of the heart tissue can cause distortion or dilation of the valvular annulus. Other diseases or malformations may result in the distortion of the cusps.

One method of repairing impaired valves is the complete surgical replacement of the valve. This method is particularly suitable when one of the cusps has been severely damaged or deformed. However, presently available artificial heart valves are not as durable as natural heart valves, and it is usually more preferable if the patient's heart valve can be left intact.

While it is difficult to retain a valve with diseased or deformed cusps, presently practiced methods provide for the ability to surgically correct dilated valve annulus. In view of the durability factor with artificial valves it is desirable to save the valve instead of performing a complete replacement.

These techniques for repairing dilated or elongated valve annulus are generally known as annuloplasty which is a surgical procedure for constraining the valve annulus dilation. In this procedure a prosthesis is sutured about the base of the valve leaflets to restrict the dilated valve annulus. The prosthesis restricts the movement of the valve annulus during the opening and closing of the valve. Prostheses used in annuloplasty are designed to provide sufficient rigidity to adequately support the valve annulus in an effort to facilitate the healing of the valve annulus, while also providing sufficient flexibility to resemble, as close as possible, the natural movement of the valve annulus during the opening and closing of the valve. This is particularly important since prosthesis are normally retained, even after the healing of the valve annulus.

Over the years different types of prostheses have been developed for use in annuloplasty surgery. In general prosthesis are annular or partially annular shaped members which fit about the base of the valve annulus against the leaflets. Initially, the prostheses were designed as rigid frame members. The initial concern was to develop a prosthesis which significantly restricted the dilation of the valve annulus. These annular prostheses were formed from a metallic or other rigid material, which flexes little, if at all, during the normal opening and closing of the valve. Examples of rigid annuloplasty ring prosthesis are disclosed in U.S. Pat. Nos. 3,656,185, issued to Carpentier on Apr. 18, 1972; and 4,164,046, issued to Cooley on Aug. 14, 1979.

Certain artificial heart valves have also been developed with rigid frame members having a rigidity similar to the rigidity of the described valve prosthesis. Examples of this type of heart valve are disclosed in U.S. Pat. Nos. 4,204,283, issued to Bellhouse et al on May 27, 1980; and 4,306,319, issued to Kaster on Dec. 22, 1981.

As stated, a rigid annuloplasty ring prosthesis adequately restricts valve dilation to promote the healing of the valve annulus. However, this rigidity prevents the normal flexibility of the valve annulus. That is, a normal heart valve annulus continuously flexes during the cardiac cycle, and a rigid ring prosthesis interferes with this movement. Since it is standard to retain the prosthesis, even after the valve annulus has healed, the rigidity of the prosthesis will permanently impair the functioning of the valve. Another disadvantage with a rigid ring prosthesis is the tendency for the sutures to become torn loose during the normal movement of the valve annulus.

Other workers have suggested the use of completely flexible annuloplasty ring prosthesis, in order to overcome the disadvantages of rigid ring prosthesis. This type of prosthesis is formed with a cloth or other very flexible material frame member. The resulting prosthesis provides little, if any resistance to the dilation of the annulus during the opening and closing of the valve. While these types of annuloplasty ring prosthesis offer increased flexibility, such prosthesis fail to correct that valve disfunction due to the dilation of the valve annulus.

Examples of completely flexible ring prosthesis are disclosed in U.S. Pat. No. 4,290,151, issued to Massana on Sept. 22, 1981, and are discussed in the articles of Carlos D. Duran and Jose Luis M. Ubago, "Clinical and Hemodymanic Performance of a Totally Flexible Prosethetic Ring for Atrioventricular Valve Reconstruction", 5 Annals of Thoracic Surgery, (No. 5), 458–463, (November 1976) and M. Puig Massana et al, "Conservative Surgery of the Mitral Valve Annuloplasty on a New AdJustable Ring", Cardiovascular Surgery 1980, 30–37, (1981).

Still other workers have suggested annuloplasty ring prosthesis which are adjustable, either during the surgical implantation, or as the ring prosthesis during the opening and closing of the valve. This type of adjustable prosthesis is typically designed in combination with a rigid, or at least partially rigid frame member. For example, the ring prosthesis taught in U.S. Pat. No. 4,489,446, issued to Reed on Dec. 25, 1984, allows for self adJustment of the prosthesis annulus by constructing the valve frame member as two reciprocating pieces. However, while the resulting prosthesis self adjusts in at least one direction, the individual frame members are formed from a rigid material. Thus the prosthesis suffers the same disadvantages as the above discussed rigid ring prosthesis.

Other examples of adjustable ring prosthesis are taught in U.S. Pat. Nos. 4,602,911, issued to Ahmadi et al and 4,042,979, issued to Angell on Aug. 23, 1977, provide for mechanism of adjusting the ring circumference. In Ahmadi et al the ring prosthesis frame is a coiled spring ribbon which is adjusted by a mechanical screw assembly. In Angell, a drawstring is used to adjust the circumference of a rigid frame member. Again, these ring prosthesis suffer from the disadvantages of the rigid ring prosthesis discussed above.

A further disadvantage with the Angell prosthesis relates to the design of the adjusting mechanism. The Angell prosthesis includes a rigid partial annular member. The open end of this member forms a gap which can be narrowed by tightening the drawstring. The tighter the drawstring is pulled the narrower the gap. The stress applied to the ring prosthesis during the opening and closing of the valve is primarily directed to the drawstring. Thus failure of the drawstring allows the prosthesis annulus to expand, allowing the valve to dilate.

It would thus be advantageous to design an annuloplasty ring prosthesis having an annular frame member which more closely reflects the naturally flexibility of the valve annulus, while providing for a sufficient degree of rigidity to resist dilation of the valve during the cardiac cycle.

An annuloplasty ring prosthesis which was designed in an attempt to provide for an elasticity closely resembling that of a natural heart valve is taught in U.S. Pat. No. 4,055,861, issued to Carpentier on Nov. 1, 1977. The annuloplasty ring prosthesis taught in Carpentier is described as being deformable, to an equal degree and simultaneously in all directions within and outside its resting plane, so as to form a skew curve. The preferred support is described as having the elasticity of an annular bundle of 2 to 8 turns of a cylindrical bristle of poly-(ethylene terephthalate). In describing the support the individual bristles may either be interwoven, or merely arranged in a side by side relationship. The extremities of the individual bristles are joined together by welding, gluing with an adhesive or ligation.

The resulting ring prosthesis of Carpentier '861 will have a single degree of flexibility, which is dependent upon the flexibility of the individual bristles, and/or the number of these individual bristles used to construct the support. Thus this device will either be rigid or completely flexible, in either case such a ring prosthesis would have the disadvantages associated with such types of ring prosthesis.

It would thus be desirable to provide a ring prosthesis which provides for a more natural flexibility of the valve annulus without suffering the above discussed disadvantages.

SUMMARY OF THE INVENTION

The present invention overcomes the above discussed disadvantages by providing a ring prosthesis which provides different flexibilities at various points about the circumference of an associated heart valve. Specifically, the annuloplasty ring prosthesis of the invention includes a segmented body formed by two or more segments. The individual segments form a body which is substantially circular and shaped proportional to fit about the annulus of the associated heart valve. The individual segments are held in position with respect to each other by a flexible joint. This flexible joint is formed by covering the segments with a flexible material which fits snugly about the segments. The cover is tied off between the adjacent segments to further restrain movement of the segments with respect to each other. In one embodiment the segments are linked together by a flexible cord. The cover may also function as a suture ring to provide a site for suturing of the prosthesis about the heart valve annulus.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a top view of one embodiment of an annuloplasty ring prosthesis, with the cloth covering being partially removed to expose the individual segments;

FIG. 2 is an enlarged view of a portion of a section of the ring prosthesis of FIG. 1 exposing some of the segments and illustrating the flexible joint and manner by which such segments are linked together using a cord; and FIG. 3 is a top view of another embodiment of an annuloplasty ring prosthesis, with the cloth covering being partially removed to expose the individual segments and the flexible joint.

DESCRIPTION OF THE PREFERRED EMBODIMENTS

The present invention is directed to annuloplasty ring prosthesis which are formed to fit about the base of the valve cusps of either a bicuspid or tricuspid valve. The ring prosthesis of the invention is formed from two or more segments which are held in position with respect to each other by a flexible joint. This flexible joint allows adjacently positioned segments to slightly bend along this joint.

When the ring prosthesis is secured in position about the valve, the individual segments move substantially independently of each other, bending at the flexible joint. By the appropriate use of different sized segments, and different number of segments, prosthesis can be designed with different degrees of flexibility about their circumference. Furthermore, by appropriately positioning the individual segments the flexibility can be positioned at those areas of the valve annulus requiring a greater degree of flexibility.

For example, it has been determined that it would be beneficial to provide a ring prosthesis having greater flexibility at those locations adjacent to that region of the valve whereat the cusps overlap. A ring prosthesis for use with a bicuspid valve can be designed with at least two portions joined together by two flexible joints. The prosthesis is then sutured about the valve annulus to position each flexible joint adjacent to the area of the valve at which the cusps overlap. The same degree of flexibility can also be achieved for a tricuspid valve by the use of at least three segment, which are appropriately joined together.

In accordance with one embodiment the ring prosthesis includes a generally rigid segment forming a substantial portion of the ring prosthesis. The remainder of the ring prosthesis is formed from small segments.

These small segments are linked together by a flexible cord, which in combination with the size of the segments provides for a very flexible portion of the ring prosthesis. This portion of the ring prosthesis would be positioned adjacent to the posterior cusp of a mitral valve. It is thus evident at a ring prosthesis of the invention can be designed to provide for flexibility along desired locations of the valve annulus.

The present invention will be described in greater detail with reference to FIGS. 1 and 2. One embodiment of a ring prosthesis of the invention is seen generally in FIGS. 1 and 2 at 10. This ring prosthesis 10 is that embodiment in which the major portion of the ring will be formed from a substantially rigid segment, with the remainder of the ring prosthesis being composed of a plurality of smaller segments.

In particular, ring prosthesis 10 includes a first substantially rigid segment 12 which defines the majority of the circumference of the ring prosthesis 10. Specifically, segment 12 is a substantially circular shaped opened ring sized to proportionally fit about a substantial portion of the annulus of the particular heart valve. In particular, segment 12 is formed to fit around about ½ to about ⅔ of the circumference of the particular heart valve annulus.

By the segment 12 being termed as substantially rigid it is meant that the ends of the segment 12, seen generally at 16 and 18, may be deflected towards each other by the application of force. The amount of flexing is dependent upon the material from which the segment is formed, and the size of the segment. The flexibility may be measured by either calculating or directly measuring the spring rate for the ring prosthesis segment 12, as determined by applying the force against the ends 16 and 18. The lower the spring rate, the greater the flexibility of the segment 12.

This spring rate may be calculated by the concept known as Finite Element Analysis. This concept involves calculating the spring rate by knowing the material from which the segment 12 is formed and also the dimensions of the segment 12. For a more detailed discuss of this concept see, "Concepts and Applications of Finite Element Analysis", Second Edition, Robert D. Cook, Department of Engineering Mechanics, University of Wisconsin-Madison, John Wiley & Sons, 1981. The smaller the segment 12, and thus the smaller the prosthesis, the greater the degree of the flexibility for the ring prosthesis. For example, a ring prosthesis of 26 millimeters would have a ring spring rate of 310 grams per millimeter, while a ring prosthesis of 38 millimeters would have a ring spring rate of 452 grams per millimeter.

As seen in FIG. 1, segment 12, which has a generally crescent shape, includes a first substantially straight section 14, and two curving end portions 16 and 18. The straight section 14 is usually dimensioned to fit along the base of the anterior cusp of an associated bileaflet heart valve, which is seen generally in phantom in FIG. 1 at 30, or along the base of the median cusp of a trileaflet heart valve, not shown. The end portions 16 and 18 are curved to fit about the heart valve annulus.

The segment 12 is preferably tapered in the direction of the end portions 16 and 18. This tapering increases the overall flexibility of the segment 12, or more precisely provides a lower spring rate.

The ring prosthesis 10 further includes a multisegmented section 32 formed from a plurality of individual segments, two of which are seen generally at 24 and 26.

These segments 24 and 26 are arranged in an end to end relationship between the ends of the segment 12. These segments 24 and 26 are linked together by at least two threads 28. As will be discussed more fully herein, these threads 28 are alternatively laced through appropriately positioned holes in each of the segments 24 and 26, and tied off in the two end segments.

While the individual segments 24 and 26 are generally cylindrical in shape, it is preferential to form the ends of adjacently positioned segments 24 and 26 with complementary shaped ends. This provides for a snug fit between such segments, while allowing for a degree of flexibility. For example, as seen in FIGS. 1 and 2, the segments 24 are formed with round concave depressions, one of which is seen at 20, into which fit a complementary formed rounded end, one of which is seen at 22, of the adjacent segment 26. The arrangement of the individual segments 24 and 26 in an end to end relationship, and linked together by the thread 28, forms the multisegmented section 32 which fits between the ends 16 and 18 of segment 12. The multisegmented section 32 is generally flexible at the junction of the individual segments 24 and 26, with the overall flexibility of the section 32 controlled by the number and dimensioning of the individual segments 24 and 26.

The tying of the segment 24 and 26 together maintains the integrity of this multisegmented section 32. In order to effect the tying of the individual segments 24 and 26 together, each segment is formed with a single hole 40, generally positioned at the mid-point of the individual segment. The threads 28 are sequentially laced through the holes 40 of adjacently positioned segments. The threads 28 are then tied off at each of the end segments, one of which is seen as segment 26 in FIG. 2.

Alternatively, single threads, not shown, may be used to tie together adjacent ones of the segments 24 and 26. Any other means of forming a similar type of multisegmented section is suitable for the purpose of the invention.

As stated, the ring prosthesis of the invention further includes hinged joints between the individual segments. In the illustrated embodiment, the multisegmented section 32 functions as a single segment, with the hinged joints being formed between this section 32 and the segment 12. The hinged joints are formed by a cloth covering 34 wrapped substantially tight about the segment 12 and section 32, with the covering being pinched together between the adjacent ends of the section 32 and segment 12. As illustrated the cover is pinched together by tightly tying a string about the cover 34 at these locations, with such tied strings being seen at 36 and 38. The cover 34 not only maintains the positioning of the section 32 between the ends of segment 12, but also provides a site for suturing the ring prosthesis about the valve annulus.

The flexible joints formed between the ends of the section 32 and segment 12 provides a degree of flexibility. Furthermore, the formation of the section 32 from the plurality of the individual segments 24 and 26 enhances the flexibility of the ring prosthesis at this location. By the appropriate dimensioning of the segment 12, and the individual segments 24 and 26, the overall flexibility and rigidity of the prosthesis 12 may be manipulated.

The segments 12, 24 and 26 may be formed from any suitable and biologically compatible material. Preferentially, the segment 12 is formed from titanium, while the individual segments 24 and 26 are formed from a plastic material, and preferably a radiopaque plastic, e.g. Delrin ®, with barium sulfate filler.

Referring now to FIG. 3, a ring prosthesis in accordance with another embodiment of the invention is seen generally at 50. Ring prosthesis 50 includes three segments 52, 54 and 56. Segment 56 is a substantially straight member, dimensioned to fit around from about ⅓ to about ½ of the circumference of the associated heart valve annulus. The two segments 52 and 54 are curved members of substantially equal length and positioned between the ends of segment 56. These three segments 52, 54 and 56 are held in position with respect to each other by a cloth covering 62, tightly wrapped about the segments 52, 54 and 56 in a manner similar to the embodiment discussed above. Furthermore, ties 64, 66 and 68 are tightly drawn about the cloth covering 62 at respective locations between the adjacently positioned segments 52, 54 and 56. This forms three hinged joints between the segments 52, 54 and 56.

The illustrated ring prosthesis 50 having three segments is particular useful for placement about a trileaflet heart valve. The larger and substantially straight segment 56 is positioned adjacent to the median cusp of the heart valve, while the remaining smaller but equivalently sized segments 52 and 54 are usually arranged adjacent to the anterior an posterior cusps of the heart valve.

In accordance with a still further embodiment, not shown, of the invention, a ring prosthesis is formed from two, substantially equivalent segments. This embodiment is particularly useful with a bileaflet heart valve, with the ring arranged about the base of the heart valve to position each of the segment adjacent to the anterior and posterior cusps.

While the preferred embodiments have been described, various modifications and substitutions may be made thereto without departing from the scope of the invention. Accordingly, it is to be understood that the invention has been described by way of illustration and not limitation.

What is claimed is:

1. An annuloplasty ring prosthesis comprising:
   a body which defines a substantially circular shaped ring proportioned to fit about the annulus of a heart valve, said body being formed from two or more segments, each of which is formed with opposing ends;
   a flexible covering fitted about said segments to position each of said segments ends adjacent to an end of another of said segments, with said ends remaining unconnected; and
   means associated with said covering for snugly holding said covering about said adjacently positioned ends.

2. The annuloplasty ring prosthesis of claim 1 wherein said individual segments are substantially rigid.

3. The annuloplasty ring prosthesis of claim 1 wherein said body is formed from three substantially equivalently sized and shaped segments.

4. The annuloplasty ring prosthesis of claim 1 wherein at least one of said segments is formed from a plurality of individual smaller elements linked together.

5. The annuloplasty ring prosthesis of claim 1 including two of said segments wherein one of said segments is substantially straight with slightly curved ends, and said second of said segments is formed from a plurality of individual smaller linked together elements.

6. The annuloplasty ring prosthesis of claim 5 wherein said smaller elements are tied together with a cord.

7. The annuloplasty ring prosthesis of claim 6 wherein each of said elements are formed with at least a first aperture through which said cord is drawn.

8. The annuloplasty ring prosthesis of claim 1 wherein said holding of said covering about said adjacently positioned segment ends is obtained by tightening said covering between said adjacent segment ends.

9. The annuloplasty ring prosthesis of claim 8 wherein said ring prosthesis includes two segments.

10. The annuloplasty ring prosthesis of claim 8 wherein said ring prosthesis includes three segments.

11. The annuloplasty ring prosthesis of claim 10 wherein a first of said segments is substantially straight, with said two other of said segments being curved.

12. The annuloplasty ring prosthesis of claim 8 wherein said ring prosthesis includes a first substantially straight segment having curved ends and a second segment formed from a plurality of linked together elements positioned between said curved ends of said first segment.

13. The annuloplasty ring prosthesis of claim 12 wherein said first segment is formed from titanium and said second segment is formed from a plastic material.

14. The annuloplasty ring prosthesis of claim 2 wherein said holding of said segment ends is obtained by tightening said covering between said adjacent segment ends.

15. The annuloplasty ring prosthesis of claim 4 wherein said holding of said segment ends is obtained by tightening said covering between said adjacent segment ends.

16. The annuloplasty ring prosthesis of claim 5 wherein said holding of said segment ends is obtained by tightening said covering between said adjacent segment ends.

17. The annuloplasty ring prosthesis of claim 16 wherein said individual elements forming said segment are oblong bodies arranged in an end to end relationship, with alternating ones of said bodies being formed with circular ends and said remaining ones of said bodies being formed with concave ends for receiving said circular element ends.

* * * * *